United States Patent [19]

Wardlaw et al.

[11] Patent Number: 4,940,668
[45] Date of Patent: * Jul. 10, 1990

[54] METHOD FOR INCREASING AGGLUTINATION OF GROUPS OF CELLS TO PRODUCE IMPROVED CELL LAYER INTERFACE IN CENTRIFUGED BLOOD SAMPLE

[75] Inventors: Stephen C. Wardlaw, Branford; Robert A. Levine, Guilford, both of Conn.; Rodolfo R. Rodriguez, Randolph, N.J.; Michael R. Loken, Los Altos, Calif.

[73] Assignee: Becton Dickinson and Company, Parsippany, N.J.

[*] Notice: The portion of the term of this patent subsequent to Sep. 22, 2004 has been disclaimed.

[21] Appl. No.: 98,370

[22] Filed: Sep. 18, 1987

Related U.S. Application Data

[63] Continuation of Ser. No. 794,127, Nov. 1, 1985, Pat. No. 4,695,553.

[51] Int. Cl.$^5$ .............................................. G01N 1/00
[52] U.S. Cl. ...................................... 436/174; 435/29; 436/17; 436/63; 436/177
[58] Field of Search ...................... 424/101; 435/29, 2; 436/63, 174, 177, 17

[56] References Cited

U.S. PATENT DOCUMENTS

| | | | |
|---|---|---|---|
| 3,902,964 | 9/1975 | Greenspan | 436/177 |
| 4,255,256 | 3/1981 | Ferrante et al. | 210/924 |
| 4,330,410 | 5/1982 | Takenaka et al. | 210/927 |
| 4,343,793 | 8/1982 | Wissler | 210/927 |

*Primary Examiner*—Sam Rosen
*Attorney, Agent, or Firm*—William W. Jones

[57] ABSTRACT

In order to produce a more well defined interface between adjacent cell layers in a centrifuged sample of anticoagulated whole blood, a material which will bond one group of cells together is added to the blood sample prior to centrifugation. The bonding material must produce a high strength bond between one group of cells, but not effect the other cell types. The material is added prior to centrifugation of the blood sample.

1 Claim, No Drawings

METHOD FOR INCREASING AGGLUTINATION OF GROUPS OF CELLS TO PRODUCE IMPROVED CELL LAYER INTERFACE IN CENTRIFUGED BLOOD SAMPLE

This application is a continuation of application Ser. No. 794,127, filed Nov. 1, 1985, now U.S. Pat. No. 4,695,553.

This invention relates to a method for providing an improved better clarified interface between the erythrocyte layer and the leukocyte layer in a centrifuged sample of anticoagulated whole blood.

U.S. Pat. No. 4,027,660 issued Apr. 2, 1976; and U.S. Pat. No. 4,082,085 issued Apr. 4, 1978 relate to a technique for performing differential leukocyte counts in a sample of anticoagulated whole blood which has been drawn into a capillary tube and centrifuged. A generally cylindrical float is disposed in the capillary tube in the blood sample during centrifugation. The float settles into the erythrocyte layer and extends through the buffy coat so as to physically elongate the leukocyte and platelet layers. A stain such as acridine orange is used to differentially color the different constituents which make up the buffy coat so that the buffy coat appears as a plurality of differently colored bands in the capillary tube. The layering constituents according to density during centrifugation allows cell counts to be made by measuring the distance between the boundaries of each cell band.

U.S. Pat. No. 4,159,896 issued July 3, 1979; and U.S. Pat. No. 4,181,609 issued Jan. 1, 1980 describe a problem, and a solution therefor, which is encountered in some blood samples tested in accordance with the above-described technique. The problem is a poorly defined demarcation between the top of the erythrocyte layer and the bottom of the leukocyte layer. The poor definition occurs because abnormally low density erythrocytes which are found in the blood sample tend to settle in the lower-most region of the leukocyte layer. The solution taught by the noted prior art is to add potassium oxalate to the blood sample to increase the density of the erythrocytes so that the less dense erythrocytes will sediment with the majority of cells in the erythrocyte layer during centrifugation. In order to accentuate the increased density, the blood sample may be warmed while in the capillary tube prior to centrifugation. Following the prior art procedure, satisfactory delineation of the erythrocyte-leukocyte boundary is achieved in approximately 98% of normal out-patient cases and in approximately 70% of the hospitalized patients. In view of the ineffectiveness of the prior art procedures in a significant number of cases, particularly in the hospital environment, it is apparent that a more efficacious procedure is desirable so that good erythrocyte-leukocyte separation would be achieved in all cases.

This invention relates to a method of achieving a clear demarcation between the erythrocytes and leukocytes in a centrifuged sample of anticoagulated whole blood in virtually every case.

The improved erythrocyte-leukocyte interface demarcation is accomplished by adding a material to the blood sample which will bond the erythrocytes together prior to centrifugation of the sample. The material which is added to the blood sample must produce a high strength bond between the erythrocytes, regardless of type, while not affecting the cells in the buffy coat. By thus agglomerating the erythrocytes prior to centrifugation, the erythrocytes will sediment according to their mean density when the sample is centrifuged. The rate of sedimentation of agglomerated cells will also be faster. Thus, the less dense microcytes and reticulocytes will not layer on top of the heavier erythrocytes, as they normally do and, therefore, will not blur the erythrocyte-leukocyte interface. The materials which are added to the blood sample are materials such as: antibodies for H red cell antigens and/or mixed A, B, H antigens; lectins (vegetable carbohydrates with antibody-like properties) such as that from *Eulex Europus*; and antibodies directed against universal erythrocyte antigens, particularly monoclonal antibodies. The preferred material is any human erythrocyte-specific monoclonal antibody which can agglutinate the target cells. Mixed lectins are also effective. Both of these materials may be combined to provide an effective additive.

The problem solved by the above-noted procedure is caused by intrusion of abnormally less dense erythrocytes into normal granulocytes. These abnormally less dense erythrocytes may be small fragments caused by poor cell formation or caused by mechanical or other damage, or may be swollen erythrocytes resulting from metabolic damage. They may also be immature erythrocytes which are known to have a lower buoyant density than mature erythrocytes. These cells are a relatively small part of the normal density population, but they may be of sufficient number to mix with and disrupt the granulocyte layer. The procedure of this invention results in an irrevocable merging of these abnormally less dense erythrocyte materials with the normal erythrocyte population. The material which is added can be characterized as a sort of "glue" specific only to erythrocytes and which converts all of the erythrocytes into small aggregates of cells of average density. Since that average density is greater than the density of the granulocytes, complete separation between the erythrocytes and the granulocytes will occur. The aggregates must not be too large to also trap leukocytes in the clusters.

When lectins are used as the agglutinating material, the following applies. Lectins such as *Eulex Europus*, *Triticum Vulgaris*, and *Phaseolus Vulgaris* may be used in this procedure and are available in powder form from Sigma Chemical Company of St. Louis, Mo. It is well known that when utilizing biologic material such as lectins, it is often impossible to specify an effective solution concentration of the biologic material, since the active constituents of the material are not known, or, are at least poorly defined. Thus, it is necessary to determine an effective concentration of the respective lectins by proceeding with sequential titrations.

A known weight or volume of the lectin material (in powder form) is dissolved in a known volume of an appropriate medium, such as saline. The initial concentration is only important as a known starting point from which an effective concentration is to be derived: Sequential titrations are then made from serial dilutions of the starting fluid. Half dilutions are recommended. This procedure is continued so as to create a range of concentrations from the original solution to the most dilute operative solution. During the progression, several drops of each dilution are mixed with an equal amount of the blood. The resulting mixtures are then examined by visual inspection for agglutination of the erythrocytes. When a minimum effective concentration or the mixture (a titre) is found, that concentration is enhanced a factor of about four to ten so as to ensure effective agglutination of the erythrocytes and economize reagents. By using an excess in this manner, possible degradation of the solution over time is negated.

As noted above, monoclonal antibodies which are specific to antigens found on all human erythrocytes, but not on leukocytes, are a preferred agglutinating material for use in the procedure of this invention. Some antigens are found on virtually all human erythrocytes. Examples of such a universal erythrocyte antigen are the H antigen and Glycophorin. The preparation and selection of anti-sera and monoclonal antibodies to these types of antigen are well known High concentrations of monoclonal antibodies can be produced as ascites fluid using standard immunological techniques. The antibody-containing ascites fluid is harvested from the mouse, and it is diluted on a one to one thousand ratio with a buffering agent. This produces the antibody-containing reagent which is used to cause the desired agglutination of the erythrocytes in the procedure of this invention.

Generally, the procedure of this invention is as follows. The erythrocyte agglutinating material is dried on the inside of a capillary tube along with stains or dyes as necessary to visually differentiate the cell layers. A sample of blood is into the coated capillary tube and the float is positioned in the capillary tube. The bottom of the tube is capped and the sample is centrifuged. A clear, even erythrocyte-leukocyte interface is achieved with no erythrocyte material rising into the leukocyte layers. The buffy coat constituents band normally so as to allow accurate measurement of band heights and thereby create accurate counts.

It will be readily appreciated that the procedure of this invention will eliminate the prior art problem of poor separation between erythrocytes and leukocytes which occurs in a significant number of tests. The additives do not affect the leukocytes and produce an even erythrocyte-leukocyte interface for accurate measurements. The erythrocytes are not prevented from buoying the float in the normal manner.

This invention can also be used to selectively agglutinated cell sub-populations to form well defined layers of such sub-populations in a centrifuged blood sample. For example, the reticulocyte sub-population of the erythrocytes can be banded separately from the remaining erythrocytes by adding a monoclonal antibody which is specific to transferrin receptors which are found on the surface of the reticulocytes. By this method, a more accurate measurement of the reticulocyte count can be achieved. This is a useful tool in the differential diagnosis of anemia, and is very time-consuming to perform by traditional methods.

The invention can likewise be used to agglutinate the eosinophil sub-population of leukocytes into a distinct band in the centrifuged blood sample by adding to the blood sample an antibody which is specific to the eosinophils. At present, the eosinophils are too dispersed throughout the granulocyte layer to be readily measured with the centrifugation procedure.

A further improvement includes the addition of a fluorescent material to the antibody used for agglutinating the cell types. For example, if the anti-transferrin receptor antibody were joined to fluorescein, the reticulocytes would be both separated and differentiated from the mass of the other erythrocytes.

Since many changes and variations of the disclosed embodiments of the invention may be made without departing from the inventive concept, it is not intended to limit the invention otherwise than as required by the appended claims.

What is claimed is:

1. A method of removing unwanted blood cell types from an assay area in a sample, said method comprising the steps of: agglutinating said unwanted blood cell types into clumps by adding an effective amount of an antibody to the sample which selectively causes increased agglutination of the unwanted blood cell types; and displacing said clumps out of said assay area of the sample.

* * * * *